United States Patent [19]
Williams et al.

[11] Patent Number: 5,398,538
[45] Date of Patent: Mar. 21, 1995

[54] ON-LINE MEASUREMENT OF ULTRASONIC VELOCITIES IN WEB MANUFACTURING PROCESSES

[75] Inventors: Paul Williams; Bradley M. Pankonin, both of Columbus, Ohio

[73] Assignee: ABB Industrial Systems Inc., Columbus, Ohio

[21] Appl. No.: 10,652

[22] Filed: Jan. 28, 1993

[51] Int. Cl.⁶ ..................... G01N 29/18; G01N 29/24
[52] U.S. Cl. ........................... 73/10 V; 73/159; 73/597
[58] Field of Search ............... 73/597, 159, 10 V

[56] References Cited

U.S. PATENT DOCUMENTS

| | | | |
|---|---|---|---|
| 4,291,577 | 9/1981 | Baum et al. | 73/597 |
| 4,509,153 | 4/1985 | Weight | 367/140 |
| 4,574,634 | 3/1986 | Pappano | 73/597 |
| 4,713,572 | 12/1987 | Bokowski et al. | 310/323 |
| 4,730,492 | 3/1988 | Burk | 73/597 |
| 4,735,087 | 4/1988 | Hourani et al. | 73/597 |
| 4,936,141 | 6/1990 | Anderson, Jr. et al. | |
| 4,950,911 | 8/1990 | Williams et al. | 256/563 |
| 4,970,895 | 11/1990 | Houghton et al. | 73/159 |
| 4,991,432 | 2/1991 | Houghton et al. | 73/159 |
| 5,013,403 | 5/1991 | Chase . | |
| 5,029,469 | 7/1991 | Chase et al. . | |
| 5,101,661 | 4/1992 | Cresson et al. . | |
| 5,104,488 | 4/1992 | Chase . | |
| 5,138,878 | 8/1992 | Cresson et al. . | |

OTHER PUBLICATIONS

Habeyer et al., "On-Line Measurement of Paper Mechanical Properties", IPC Technical Paper Series, No. 157, Aug. 1985.

Martin et al., "Back-Face Only Electrical Connections of Thickness Mode Piezoelectric Transducers", IEEE Transactions on Ultrasonics, Ferroelectric, Frequency Control vol. UFFC–33, No. 6, Nov. 1986.

*Primary Examiner*—Hezron E. Williams
*Assistant Examiner*—Rose M. Finley
*Attorney, Agent, or Firm*—Killworth, Gottman, Hagan & Schaeff

[57] ABSTRACT

The velocity or speed of ultrasonic energy in moving webs of material is measured on-line as the webs are manufactured by engaging and preferably scanning a measuring head over the web of material. Improved ultrasonic energy transducers are employed wherein a material contacting member is secured to an interface region between oppositely operated first and second regions which intensify and amplify the movement of the interface region and hence the material contacting member by operating in a push-pull mode relative to the interface region. The transducers are calibrated by means of reference paths having known ultrasonic transmission characteristics which reference paths are separate and apart from the web of material which is being measured. The transducers can be selectively contacted with the web of material or not under the influence of vacuum which is applied to a measuring head into which the transducers are installed. A large plurality of ultrasonic energy signals are received by one or more receiving transducers and digitally integrated or summed and averaged to eliminate substantial noise which is present on the received ultrasonic energy signals due to the relative motion of the transducers and the web of material being measured. The travel time between the transmitting transducer and the receiving transducer or transducers is then combined with the distance or distances therebetween to arrive at the velocity or speed of the ultrasonic energy in a web being measured.

12 Claims, 6 Drawing Sheets

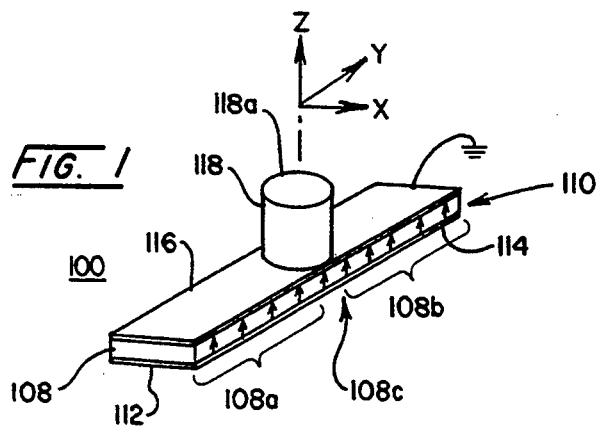
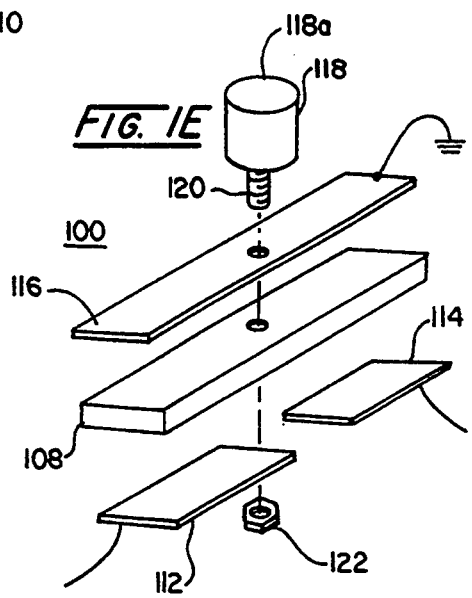
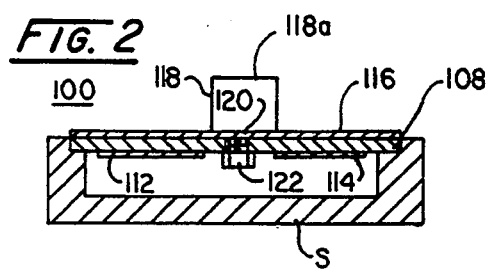
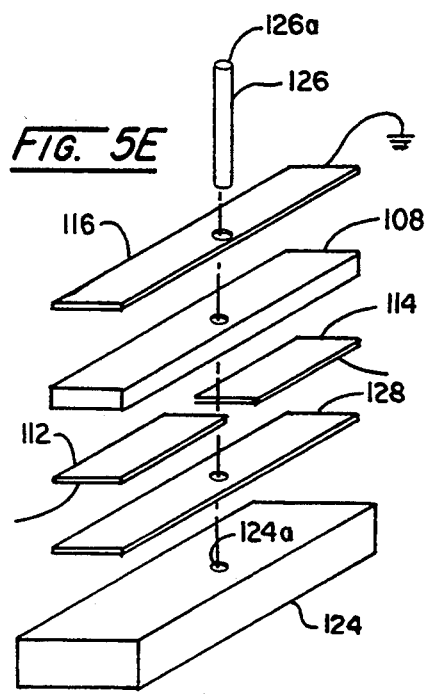
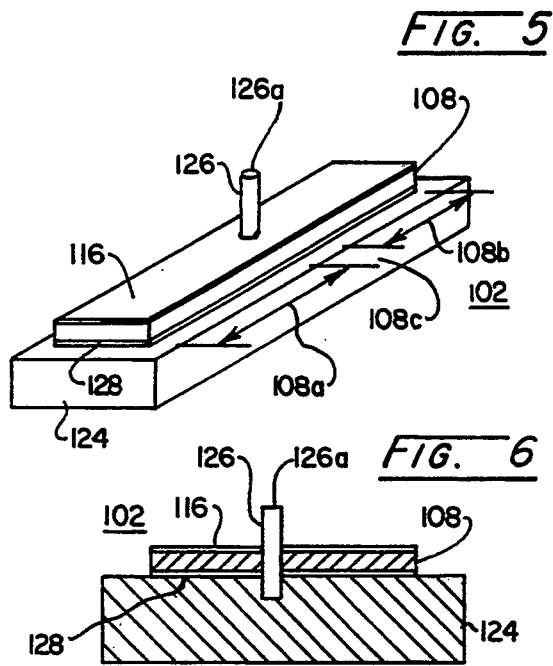
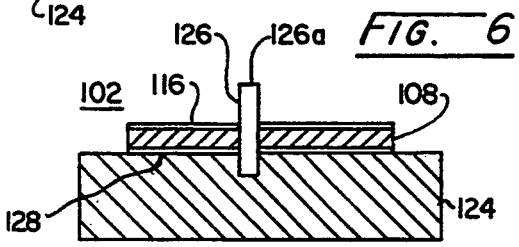

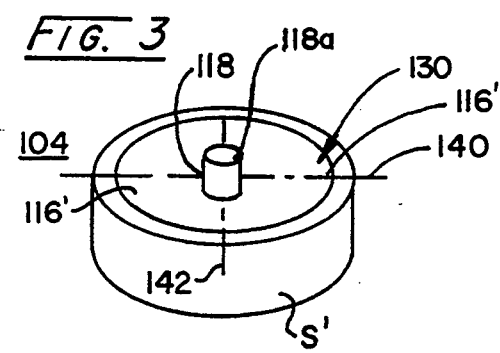
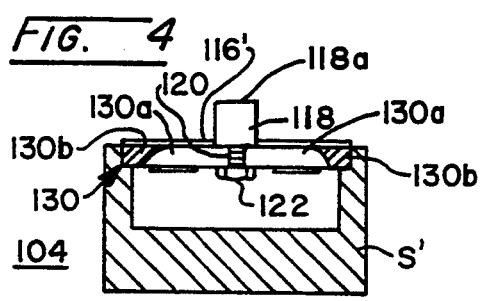
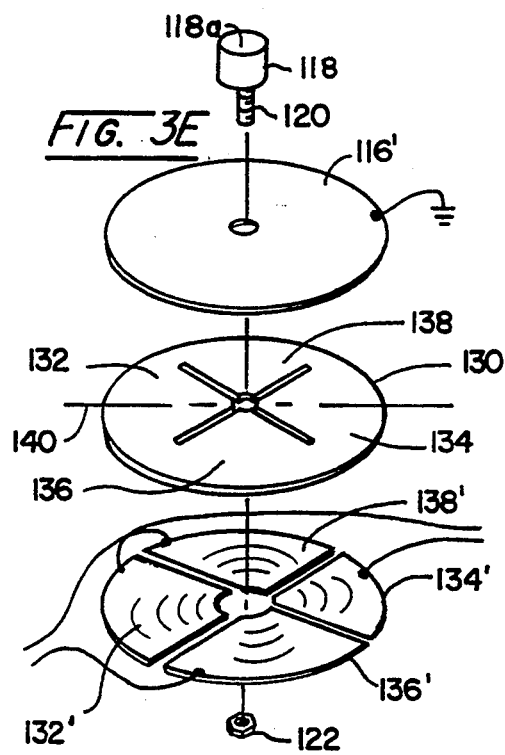
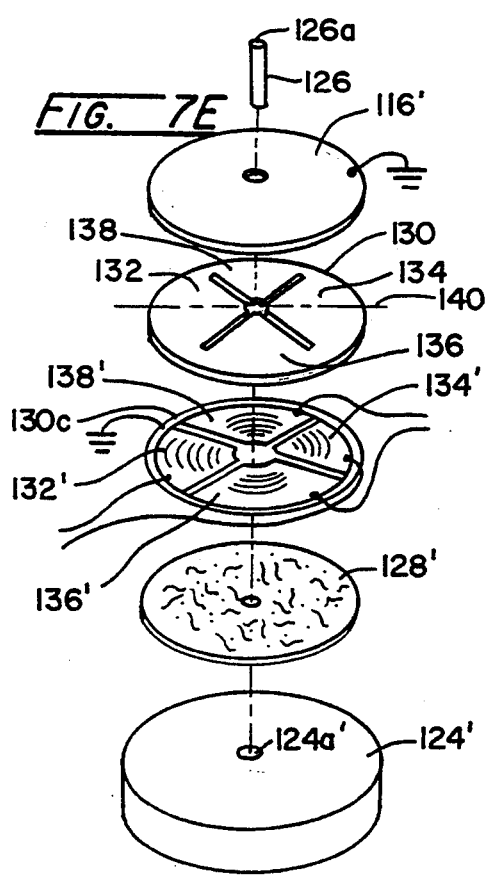
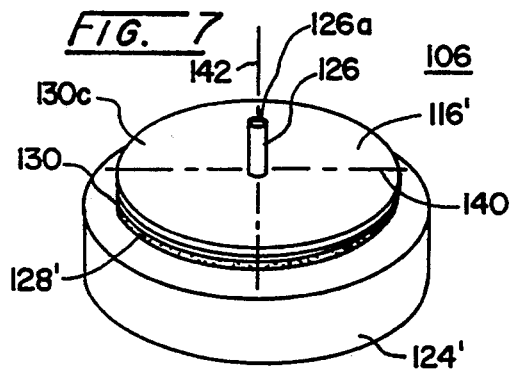
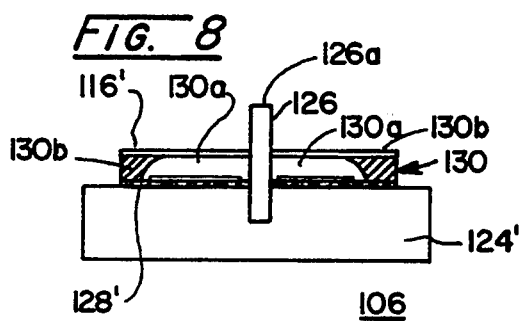

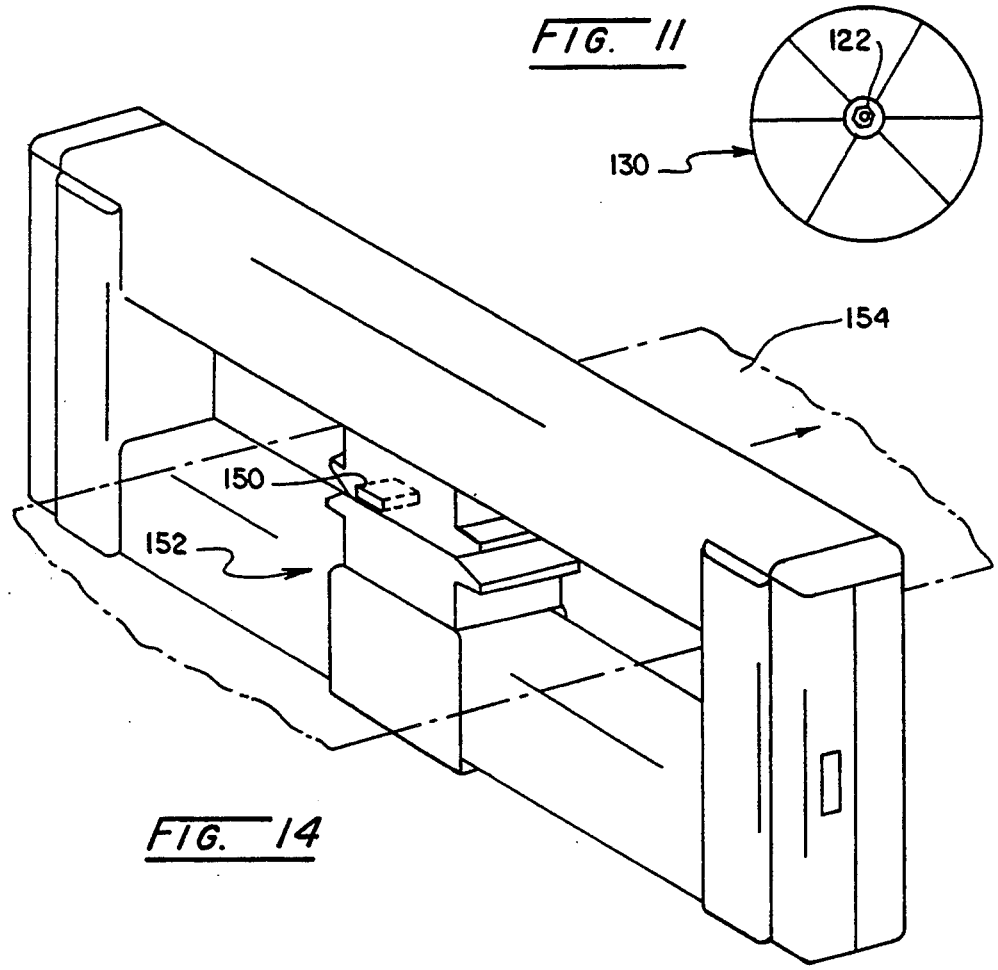
FIG. 11
FIG. 14
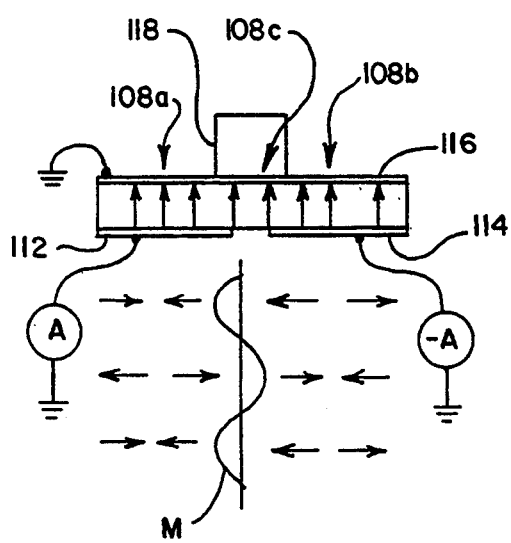
FIG. 9
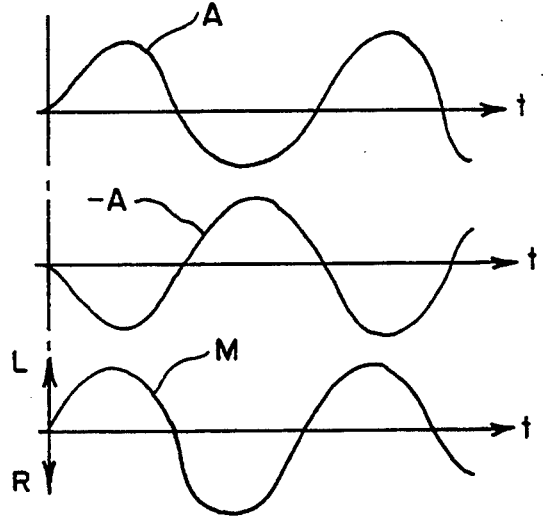
FIG. 10

ON-LINE MEASUREMENT OF ULTRASONIC VELOCITIES IN WEB MANUFACTURING PROCESSES

BACKGROUND OF THE INVENTION

The present invention relates generally to on-line measurement of properties of sheet material as the sheet material is being manufactured and, more particularly, to methods and apparatus for measuring mechanical properties of webs of sheet material as the webs are being manufactured by measuring the propagation speed of ultrasonic energy through the webs. While the present invention-can be applied to webs of a variety of materials, it is particularly applicable and has been initially developed for use with webs of paper and, accordingly, will be described with reference to this application.

Measurement of the speed or velocity of propagation of ultrasonic energy in paper sheets is well known as a nondestructive test for predicting the mechanical strength of paper sheets and other structures Constructed from paper sheets, see, for example, U.S. Pat. No. 4,574,634 which is incorporated herein by reference. Many manufacturers have replaced less sophisticated destructive tests with such nondestructive tests and routinely perform the nondestructive ultrasonic energy tests on samples of finished paper products. Unfortunately, as long as the ultrasonic tests are performed off-line on finished paper products, substantial amounts of defective product may be produced before it has even been determined that the product is defective.

To correct this problem, on-line testing using ultrasonic energy has been pursued. See, for example, U.S. Pat. Nos. 4,291,577 and 4,730,492 which are incorporated herein by reference. These on-line testing arrangements utilize rotating wheels or drums having surface mounted transducers which are rotated with a web of paper such that there is effectively no relative motion between the transducers and the web being tested. Two or three transducers are oriented on the drums or wheels to make substantially simultaneous contact with the web of paper.

An impulse of ultrasonic energy is generated at a transmitting transducer when the transducers are in contact with the web. The impulse is then detected at a second receiving transducer or second and third receiving transducers. The velocity of the ultrasonic energy through the web is then calculated using the arrival time or arrival time difference if three transducers are used) and the distance between the transducers. Three transducers were provided in an attempt to remove timing errors introduced into the calculated velocities by phase shifts in the electrical and mechanical interactions of the transducers.

Unfortunately, none of the ultrasonic energy on-line testing arrangements pursued to date has resulted in a practical commercial measurement for webs of paper or other materials as they are being manufactured. Accordingly, a need remains for an accurate and reliable testing arrangement to determine mechanical properties of webs of sheet material as the webs are being manufactured by measuring the propagation speed of ultrasonic energy through the webs. Preferably such an arrangement would tolerate relative motion between ultrasonic transducers and webs of material being measured for association with conventional web scanning equipment.

SUMMARY OF THE INVENTION

This need is met by the methods and apparatus of the present invention wherein the velocity or speed of ultrasonic energy in moving webs of material is measured on-line as the webs are manufactured by engaging and preferably scanning a measuring head over the web of material. The additional noise generated by relative motion between ultrasonic transducers in the measuring head and the web of material due to the motion of the web and/or scanning the head over the web can be overcome in accordance with the present invention to substantially simplify the testing apparatus.

Improved ultrasonic energy transducers are employed wherein a material contacting member is secured to an interface region between oppositely operated first and second regions which intensify and amplify the movement of the interface region and hence the material contacting member by operating in a push-pull mode relative to the interface region The transducers are calibrated by means of reference paths having known ultrasonic transmission characteristics which reference paths are separate and apart from the web of material which is being measured. The transducers can be selectively contacted with a moving web of material or not under the influence of vacuum which is applied to the measuring head into which the transducers are installed.

The transducers are initially calibrated using an interconnecting reference path. A single transducer can be used to transmit ultrasonic energy through a web with the resulting ultrasonic energy being received by one, two or more transducers to determine the velocity of one, two or more modes of ultrasonic energy waves in the plane of the web. In an illustrated embodiment of the invention, the velocity of ultrasonic longitudinal waves and ultrasonic shear waves are measured using a first transmitting transducer, a second receiving transducer and a third receiving transducer. A fourth receiving transducer is illustrated and can be used to receive combined ultrasonic longitudinal and shear waves, if desired, for example to provide redundancy.

An ultrasonic energy signal made up of a selected number of cycles of a selected frequency is transmitted to a transmitting transducer. A large plurality of such ultrasonic energy signals are received by one or more receiving transducers and digitally integrated or summed and averaged to eliminate the substantial noise which is present on the received ultrasonic energy signals due to the relative motion of the transducers and the web of material being measured. The travel time between the transmitting transducer and the receiving transducer or transducers is then combined with the distance or distances therebetween to arrive at the velocity or speed of the ultrasonic energy in a web being measured.

In accordance with one aspect of the invention, a transducer for transmitting ultrasonic energy through sheet material and/or receiving ultrasonic energy therefrom comprises piezoelectric means having at least first and second portions which interface with one another at an interface region for generating and/or receiving the ultrasonic energy. Material contact means couple the piezoelectric means to the sheet material with the material contact means being secured to the interface region of the piezoelectric means. Electrical contact means are provided for making an electrical connection to the at least first and second portions of the piezoelectric means.

The piezoelectric means may comprise a bar of piezoelectric material, approximately a first half of the bar defining the first portion of the piezoelectric means and approximately a second half of the bar defining the second portion of the piezoelectric means. The interface region of the piezoelectric means comprises a central portion of the bar extending between the first and second portions. The electrical contact means may comprise a first contact electrically connected to the first half of the bar and a second contact electrically connected to the second half of the bar. The electrical contact means preferably comprises an electrode film deposited on the bar with the electrode film being removed over the interface region to separate and define the first and second contacts. To dampen extended ultrasonic oscillations beyond termination of an ultrasonic driving signal, preferably a dimension of the material contact means between the piezoelectric means and the material is made equal to approximately one quarter wavelength of the ultrasonic energy.

Alternately the piezoelectric means may comprise a disc of piezoelectric material, approximately a first half of the disc defining the first portion of the piezoelectric means and approximately a second half of the disc defining the second portion of the piezoelectric means. The interface region of the piezoelectric means comprises a diametric portion of the disc extending between the first and second portions with the material contact means being secured to a central portion of the interface region approximately at the center of the disc and extending axially therefrom.

For this embodiment, the electrical contact means comprises a first contact electrically connected to the first half of the disc and a second contact electrically connected to the second half of the disc. The interface region may be defined by at least partially cutting through the disc along the diametric portion of the disc. The interface region is defined at least in part by cutting through a central part of the disc along the diametric portion thereof, the central part extending between two opposite edges of an annular ring of the disc which annular ring maintains the integrity of the disc. The first and second contacts are separate from the annular ring and the contact means may further comprise an annular contact substantially corresponding and electrically connected to the annular ring.

To further enhance movement of the interface region, the transducer may further comprise support means for supporting the piezoelectric means and for restraining movement of the at least first and second portions of the piezoelectric means spaced from the interface region.

More than two portions may be defined for a transducer. For example, the piezoelectric means may have at least first, second, third and fourth portions, the first and second portions being on opposite sides of the interface portion and being linearly aligned with one another, and the third and fourth portions being on opposite sides of the interface portion and being linearly aligned with one another, the first and second portions being angularly oriented relative to the third and fourth portions. For this embodiment, the electrical contact means further provides for making electrical connection to the third and fourth portions. For a four portion transducer, preferably the first and second portions are oriented at a 90° angle relative to the third and fourth portions.

Alternately, the piezoelectric means may have first, second, third and fourth portions which interface with one another at the interface region, the piezoelectric means comprising a disc of piezoelectric material, approximately a first quarter of the disc defining the first portion of the piezoelectric means and approximately a second quarter of the disc diametrically opposite to the first quarter defining the second portion of the piezoelectric means, approximately a third quarter of the disc defining the third portion of the piezoelectric means and approximately a fourth quarter of the disc diametrically opposite to the third quarter defining the fourth portion of the piezoelectric means. The interface region of the piezoelectric means comprises a central portion of the disc extending between the first, second, third and fourth portions. The electrical contact means comprises a first contact electrically connected to the first quarter of the disc, a second contact electrically connected to the second quarter of the disc, a third contact electrically connected to the third quarter of the disc, and a fourth contact electrically connected to the fourth quarter of the disc. Preferably, the contact means comprises an electrode film deposited on the disc, the electrode film being removed over the interface region and between the first, second, third and fourth portions of the piezoelectric means to separate and define the first, second, third and fourth contacts. The transducer may further comprise support means for supporting the piezoelectric means and the material contact means. For this embodiment, the material contacting means comprises rod means rigidly secured by the support means and extending through and a defined distance beyond the piezoelectric means.

In accordance with another aspect of the present invention, apparatus for on-line measurement of velocities of ultrasonic energy in sheet material comprises a first transducer for transmitting ultrasonic energy through the sheet material during manufacture of the sheet material and a second transducer for receiving ultrasonic energy from the sheet material during manufacture of the sheet material. Housing means supports the first and second transducers in a defined orientation relative to one another for engagement with the sheet material during manufacture. First reference path means are coupled between the first transducer and the second transducer for providing a reference path having known ultrasonic energy transmission characteristics between the first and second transducers.

The apparatus may further comprise a third transducer for receiving ultrasonic energy from the sheet material during manufacture of the sheet material, the housing means further providing for supporting the third transducer in a defined orientation relative to the first and second transducers for engagement with the sheet material during manufacture thereof. Second reference path means are coupled between the first transducer and the third transducer for providing a reference path having known ultrasonic energy transmission characteristics between the first and third transducers. The housing means comprises air bearing means for supporting the housing on the sheet material and engagement means for selectively engaging the first, second and third transducers with the sheet material. The engagement means may comprise vacuum application means for drawing the sheet material to the first, second and third transducers.

The apparatus preferably further comprises driver means for driving the first transmitter means to transmit a selectable number of cycles of defined frequency ultrasonic energy and receiver means for receiving signals representative of the ultrasonic energy from the second and third transducers and identifying the selectable number of cycles of the defined frequency ultrasonic energy.

In accordance with yet another aspect of the present invention, a method of on-line measurement of velocities of ultrasonic energy in sheet material comprises the steps of: (a) providing a first transducer for transmitting ultrasonic energy through sheet material as the sheet material is being manufactured; (b) providing a second transducer for receiving ultrasonic energy from the sheet material, the second transducer being positioned a known distance from the first transducer; (c) calibrating the first and second transducers via a reference path coupled therebetween to determine a time of origination of ultrasonic energy transmitted through the sheet material by the first transducer, the reference path having known ultrasonic energy transmission characteristics; (d) engaging the first and second transducers with the sheet material as it is being manufactured; (e) transmitting a selected number of cycles of defined frequency ultrasonic energy through the sheet material via the first transducer; (f) receiving the selected number of cycles of defined frequency ultrasonic energy from the sheet material via the second transducer; (g) determining the time of receipt of an origination point of the selected number of cycles of defined frequency ultrasonic energy; and, (h) determining the velocity of the ultrasonic energy from the known distance of the second transducer from the first transducer and the origination point of the selected number of cycles of defined frequency ultrasonic energy.

The step (c) of calibrating the first and second transducers via a reference path coupled therebetween preferably comprises the steps of: (i) transmitting a Selected number of cycles of defined frequency ultrasonic energy through said reference path via said first transducer; (j) receiving said selected number of cycles of defined frequency ultrasonic energy from said reference path via said second transducer; and, (k) determining the time of receipt of an origination point of said selected number of cycles of defined frequency ultrasonic energy.

It is thus an object of the present invention to provide improved methods and apparatus for on-line measurement of the velocity or speed of ultrasonic energy in webs of material as the webs are being manufactured; to provide improved methods and apparatus for on-line measurement of the velocity or speed of ultrasonic energy in webs of material as the webs are being manufactured wherein improved ultrasonic energy transducers are employed; to provide improved methods and apparatus for on-line measurement of the velocity or speed of ultrasonic energy in webs of material as the webs are being manufactured wherein transducers are calibrated by means of one or more reference paths which are separate and apart from the webs of material which are being measured; and, to provide improved methods and apparatus for on-line measurement of the velocity or speed of ultrasonic energy in webs of material as the webs are being manufactured wherein noise due to relative movement between webs of material and ultrasonic transducers is substantially eliminated by collecting a large number of samples and digitally integrating those samples. Other objects and advantages of the invention will be apparent from the following description, the accompanying drawings and the appended claims.

BRIEF DESCRIPTION OF THE DRAWING

FIG. 1 is a perspective view Of a first embodiment of an improved ultrasonic transducer of the present invention;

FIG. 1E is an exploded view of the transducer of FIG. 1;

FIG. 2 is a cross sectional view of the transducer of FIG. 1 additionally showing a transducer support housing;

FIG. 3 is a perspective view of a second embodiment of an improved ultrasonic transducer of the present invention having a circular piezoelectric element, see drawing sheet 2;

FIG. 3E is an exploded view of the transducer of FIG. 3;

FIG. 4 is a cross sectional view of the transducer of FIG. 3;

FIG. 5 is a perspective view of a third embodiment of an improved ultrasonic transducer of the present invention;

FIG. 5E is an exploded view of the transducer of FIG. 5;

FIG. 6 is a cross sectional view of the transducer of FIG. 5;

FIG. 7 is a perspective view of a fourth embodiment of an improved ultrasonic transducer of the present invention having a circular piezoelectric element, see drawing sheet 2;

FIG. 7E is an exploded view of the transducer of FIG. 7;

FIG. 8 is a cross sectional view of the transducer of FIG. 7;

FIG. 9 is a schematic view of a piezoelectric element illustrating operation of a transducer in accordance with the present invention;

FIG. 10 is a series of graphs representing electrical drive signals for the piezoelectric element of FIG. 9 and the resulting motion of an interface portion;

FIG. 11 is a schematic plan view of a fifth embodiment of an improved ultrasonic transducer of the present invention;

FIG. 14 is a perspective view of a conventional measuring or gauging system into which the present invention is preferably incorporated for performing ultrasonic measurements on moving webs of material as they are being manufactured, see drawing sheet 3;

DETAILED DESCRIPTION OF THE INVENTION

Figure 12:
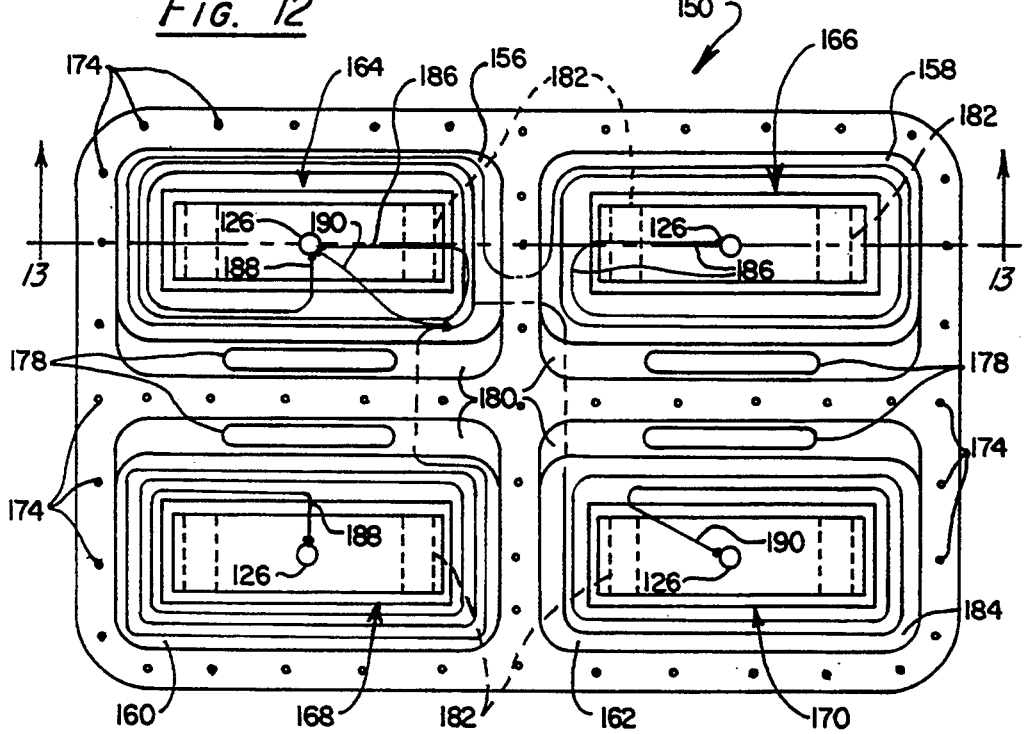
FIG. 12 is a bottom view of a measuring head for performing ultrasonic measurements on moving webs of material in accordance with the present invention.

In previous attempts at performing on-line testing of webs of material using ultrasonic energy, transducers were placed on the periphery of wheels or drums. The wheels or drums were then engaged with and rotated on the moving web of material such that the transducers periodically contacted the web and did not move substantially relative to the web during contact. Ultrasonic measurements were made during the time that both transmitting and receiving transducers were simultaneously in contact with the web.

Taking ultrasonic measurements at approximately zero relative velocity between the transducers and a web being measured substantially reduces mechanical noise which is otherwise produced by moving the transducers relative to the web. However, rotating wheels or drums substantially increase the complexity of measuring apparatus as is apparent from the later two of the above referenced patents. Further, it is very difficult if not impossible to incorporate such rotating measurement systems into a conventional web scanner which/is routinely used to measure other characteristics of webs of material as they are being manufactured, for example, basis weight in the case of paper webs.

In spite of reduced noise levels due to synchronous rotation of transducers with a web to be measured and low noise optical signal coupling to the transducers, known ultrasonic web measurement systems have been unable to provide reliable on-line measurements of web processes. In part the problems encountered in utilizing these ultrasonic measurement systems were due to low ultrasonic signal levels associated with the transducers used to transmit ultrasonic energy to the web and receive ultrasonic energy from the web. In addition, variables inherent in the transducers and the interfaces of the transducers to the web were not properly compensated in the known measurement systems.

In an attempt to correct errors in measurements made with systems using two transducers, a third transducer was added. For measurements made using three transducers, one transducer transmitted ultrasonic energy while the second and third transducers received the ultrasonic energy after traveling through a web whose characteristics were to be measured. The second and third receiving transducers were positioned at different distances from the first transmitting transducer. The travel time from the first transmitting transducer to the second and third receiving transducers was used to calculate travel time of the acoustic energy in the web. The electrical delays in the circuitry and electro-acoustic delays in the transducers were to be compensated by subtracting the propagation time to the nearer of the receiving transducers from the propagation time to the farther of the receiving transducers.

While this approach appears correct, it does not account for differences in the transducers, which can be significant even for identically prepared transducers, or differences in the interfaces between the individual transducers and the web. Transducer differences and transducer interfaces also vary over time and in response to their environment and these variations are not uniform from transducer to transducer. Further, the path traveled to the second and third receiving transducers are not identical to one another. Accordingly, even if the transducers and transducer/web interfaces are identical, the effective electro-acoustic delays in the transducers could not be eliminated by subtracting the travel time of the acoustic energy to the nearer of the receiving transducers from the travel time to the farther of the receiving transducers.

Applicants have recognized that the transducers and associated electronics need to be calibrated over an ultrasonic path having known characteristics rather than through the web which is being measured. To perform this calibration, a reference path is interconnected between a transmitting transducer and each of one or more receiving transducers. The transducers can then be calibrated to compensate for differing characteristics of the transducers.

To further improve accuracy for the on-line measurement methods and apparatus of the present invention, a selected number of cycles of the ultrasonic energy is transmitted by the transmitting transducer such that the frequency and number of cycles can be used to assist in verifying the presence of transmitted ultrasonic energy at the receiving transducers and the point in time of the origin or onset of receipt of that ultrasonic energy. The beginning point in time of the transmitted ultrasonic energy is determined by identifying the frequency and number of cycles of ultrasonic energy received by a receiving transducer over a calibration reference path, with calibration being periodically performed. The beginning point of the received ultrasonic energy as transmitted in-plane through the web of material to be measured is then determined by identifying the frequency and number of cycles of the ultrasonic energy received by the receiving transducer.

The travel time can then be accurately determined within limits determined by variations in the interfaces between the transducers and the web. The transmission of a selected number of cycles of known frequency ultrasonic energy signals permits analysis of ultrasonic energy signals received by a transducer. Discrepancies between the received ultrasonic energy signals and the known transmitted signals alert the system to changes which can be induced by variations in the interfaces between the transducers and the web or by external noise. If the discrepancies are sufficiently large, a received signal is rejected as being corrupt. Discrepancies in acceptably received ultrasonic energy signals are suggestive of corrections which can be made to further improve accuracy of measurements made in accordance with the invention. Knowing the travel time and the distance between the transmitting transducer and the receiving transducer or transducers, the corresponding velocity or velocities of the ultrasonic energy can be determined readily.

By utilizing improved transducers and operating the transducers in accordance with the methods of the present invention, accurate measurements of the velocity of ultrasonic energy in moving webs of material can be determined as the webs are being manufactured without requiring the complicated and cumbersome rotating wheels or drums of previously proposed online measuring systems. The improved transducers are incorporated into a measuring head which is supported upon and separated from the moving web of material by compressed air which is ejected through air bearing surfaces of the measuring head.

The transducers which are contained within the head selectively engage the web as it passes over the measuring head under the control of vacuum which is applied for contact and released for noncontact. It is presently preferred to bring all transducers into contact with the web or to remove all transducers from contact with the web; accordingly, selective contact as used herein is for all transducers. However, in some applications it may be preferred to bring only two transducers into contact with the web at one time. If contact is limited to two transducers at a time, the possibility of reflections from one transducer interfering with the receipt of ultrasonic energy signals by another transducer is eliminated or reduced.

A single measuring head can be moved across a moving web of material to measure characteristics of the web or a series of measuring heads can be provided across a web. Since the measuring head can be moved across a moving web of material while performing measurements, a single measurement head can be incorporated into or otherwise associated with a conventional web scanner which is routinely used to measure other characteristics of webs of material as they are being manufactured, for example the basis weight of paper webs.

Improved transducers for transmitting and/or receiving ultrasonic energy will now be described with reference to FIGS. 1–8. The first embodiment 100 and third embodiment 102 of FIGS. 1 and 5 are constructed using a generally rectangular bar of piezoelectric material such as PZT (lead zirconate titanate); and, the second embodiment 104 and fourth embodiment 106 are constructed of a generally circular disc of piezoelectric material. Improved transducers in accordance with the present invention utilize piezoelectric means for generating and/or receiving ultrasonic energy. In the later described applications of the illustrated transducer embodiments, each transducer serves as either a transmitter or a receiver; however, it is possible to utilize a single transducer as both a transmitter and a receiver in accordance with the present invention.

The piezoelectric means of all of the illustrated embodiments operate in a similar manner. Accordingly, for ease of illustration and description, the operation of the piezoelectric means will be described with reference to the embodiment of FIG. 1. Once understood, the operation of multiple pairs of portions of piezoelectric material will be apparent, and two pairs will be described with reference to the embodiments of FIGS. 3–4 and 7–8.

As shown in FIGS. 1 and 1E, a generally rectangular bar 108 of piezoelectric material is entirely polarized in one direction, for example as shown by the arrows 110. The bar 108 has a first portion 108a and a second portion 108b which interface one another at an interface region 108d. Electrical contact means comprising electrical contacts 112, 114 are provided for making an electrical connection to the lower surfaces of the first and second portions 108a, 108b of the bar 108 of piezoelectric material. It is noted that different polarizations can be used for the first and second portions 108a, 108b provided drive signals and signal handling procedures are appropriately adapted.

In the illustrated embodiment, the contact means also includes an electrical contact 116 on the lower surface of the bar 108. To reduce noise, the contact 116 is preferably connected to ground potential; however, it can be allowed to float if desired. The contacts 112, 114, 116 are preferably formed by depositing an electrode film on the corresponding surfaces of the bar 108. The contacts 112, 114 can be formed from a single deposition by removing the electrode film over the transducer portion 108c of the bar 108.

Material contacting means comprising a cylindrical stud 118 in the embodiment of FIGS. 1–4, provides for coupling the bar 108 of piezoelectric material to a web of sheet material, the characteristics of which are to be measured. The stud 118 is secured to the interface region 108c of the bar 108 by means of a threaded extension 120 and a nut 122 as shown in FIGS. 1E and 2.

To transmit ultrasonic energy through a web of material, the top 118a of the stud 118 is placed in contact with a web of material to be measured and the contacts 112, 114 are driven with oppositely phased signals A, −A such that as the signal on the contact 112 is increasing the signal on the contact 114 is decreasing and vice versa as shown in FIGS. 9 and 10. When a portion of the bar 108 of piezoelectric material is driven by a negative signal, it expands with the volume remaining constant. Conversely, when a portion of the bar 108 is driven by a positive signal, it contracts with the volume remaining constant.

Accordingly, as the oppositely phased signals A, −A drive the first and second portions 108a, 108b of the bar 108 of piezoelectric material, the interface portion 108c is pushed by one portion and pulled by the other to intensify and expand the motion of the interface portion 108c and consequently the motion M of the stud 118 which is secured to the interface portion 108c. As shown in FIG. 2, the transducer 100 may further comprise support means S for supporting the bar 108. The motion M of the interface portion 108c and hence the stud 118 may be further enhanced by thus supporting the bar 108 and thereby restraining movement of the ends of the bar 108.

A bar 108 of piezoelectric material is also used in the third embodiment of FIGS. 5–6. For ease of description and identification, elements of the third embodiment which are the same as or have corresponding elements in the first embodiment will be identified by the same identifying numerals. In this embodiment, the material contacting means comprises rod means for levered amplification of the motion of the bar 108. This embodiment includes a generally rectangular base means comprising a brass block 124 as illustrated for supporting the bar 108 of piezoelectric material and the rod means.

The rod means comprises a section of stainless steel dowel 126 with the top 126a of the dowel 126 being placed in contact with a web of material to be measured. The dowel 126 is secured in a receiving opening 124a of the block 124 and the bar 108 is secured to the block 124 by means of a layer 128 of epoxy or other appropriate adhesive or securing means. The dowel 126 thus serves as a lever with the bar 108 of piezoelectric material serving as a moving fulcrum to multiply the motion of the top 126a of the dowel 126.

The push-pull operation which amplifies the motion of the interface region of the piezoelectric bar 108 or other two portion configuration of piezoelectric material when operating as a transmitter also improves the performance of a transducer when operated as an ultrasonic receiver. Signals generated by the piezoelectric material are received from the contacts 112, 114, and preferably differentially processed. If an axial force, a force in the z-direction as shown in FIG. 1, is applied to the stud 118 or the dowel 126, approximately the same level of signal is generated on each of the contacts 112, 114 such that there is no differential signal generated. Also, approximately the same level of signal is generated on the contacts 112, 114 for forces applied in the x-direction.

However, for forces applied in the y-direction or in alignment with the bar 108 or two portions of piezoelectric material, a differential signal is generated across the contacts 112, 114. The generation of a differential signal on the contacts 112, 114 can be best understood by noting that a force in the y-direction tends to place One portion of the bar 108 of piezoelectric material into compression and the other portion into expansion. Thus, when used as a differential receiver, the transducers of the present invention are selective in terms of the direction of the applied forced to-which they best respond thereby reducing unwanted signals otherwise generated and possibly interfering with accurate measurements.

It should be apparent that the first and third embodiments share common piezoelectric elements as do the second and fourth embodiments, while the first and second embodiments share common material contact means as do the third and fourth embodiments. Accordingly, common elements of the four transducer embodiments will be identified using the same numerals for ease of description and identification. Corresponding elements which are generally circular or disc shaped as opposed to being generally bar shaped will be identified by the same numeral with a prime (') to distinguish the two. The second embodiment 104 of FIGS. 3–4 and the fourth embodiment 106 of FIGS. 7–8 comprise a disc 130 of piezoelectric material.

Each piezoelectric disc 130 comprises first and second portions 132, 134 and third and fourth portions 136, 138. Separate electrical connections are made to the first, second, third and fourth portions 132–138 by means of electrical contact means comprising first, second, third and fourth contacts 132'–138' which substantially cover the lower surfaces of the first, second, third and fourth portions 132–138. The first, second, third and fourth contacts 132'–138' preferably are formed by depositing an electrode film and then removing the film to define sectors which in turn define the first, second, third and fourth contacts 132'–138'. The interface portion of each piezoelectric disc 130 is the central portion of the disc 130 and the material contacting means is secured to the interface portion in the same manner as described above relative to the first and third embodiments of FIGS. 1–2 and 5–6 as should be apparent from FIGS. 3–4 and 7–8.

To enhance movement of the first and second portions 132, 134 and the third and fourth portions 136, 138, preferably they are defined by partially cutting through the disc 130 along diametric sections of the disc 130 which separate the portions from one another. As shown in FIGS. 4 and 8, the cuts 130a are through a central part of each disc 130 and extend between an annular ring 130b which maintains the integrity of each disc 130. The cuts can be made by plunge cutting using a circular saw as suggested by the arcuate ends of the cuts 130a.

If an electrode film is used to define the contacts 132'–138' on the lower surface of each disc 130, then the remainder of each diametric section is defined by removing the film which otherwise covers the annular ring 130b. If desired and as illustrated in FIG. 8, the lower surface of the annular ring 130b may be covered by a separate electrode 130c formed from an electrode film or otherwise and connected to ground to reduce noise within the system.

The first and second portions 132, 134 operate as previously described with reference to the bar 108 of FIG. 1 to transmit ultrasonic energy through a web of material and/or to receive ultrasonic energy from a web of material. Electrical activation of the first and second portions 132, 134, causes motion of the material contact means along a diameter 140 which generally bisects the sectors or portions 132, 134, see FIGS. 3, 3E, 7 and 7E. This motion generates substantially pure longitudinal waves in alignment with the diameter 140 and substantially pure shear waves perpendicular thereto, with proportional mixtures of longitudinal and shear waves in directions therebetween. Differential signals are also generated on the contacts 132', 134' of the first and second portions 132, 134 for ultrasonic energy inducing motion of the material contact means along the diameter 140.

In a similar manner, electrical activation of the third and fourth portions 136, 138, causes motion of the material contact means along a diameter 142 which generally bisects the sectors or portions 136, 138, see FIGS. 3 and 7. This motion generates substantially pure longitudinal waves in alignment with the diameter 142 and substantially pure shear waves perpendicular thereto with proportional mixtures of longitudinal and shear waves in directions therebetween. Differential signals are also generated on the contacts 136', 138' of the first and second portions 136, 138 for ultrasonic energy inducing motion of the material contact means along the diameter 142.

It should be apparent that the disc 130 can be divided into more than two pairs of opposite segments or portions if substantially pure longitudinal and/or shear ultrasonic energy waves are to be coupled through a web of material and/or received from a web of material in more than the two directions generally defined by the diameters 140, 142. See for example, FIG. 11 wherein three pairs of sectors or portions are defined on a piezoelectric disc 130. In addition, the form and direction of ultrasonic energy waves can be varied electrically by phase changes of the signals used to drive the transducers. In this way, longitudinal and/or shear energy waves can be transmitted in substantially any direction using transducers having piezoelectric elements having only two portions. Such configurations and/or operations may be preferred in some applications to reduce the number or complexity of transducers.

Further, while the transducers have been described as being constructed of a single bar or disc of piezoelectric material, each transducer can be constructed from two or more piezoelectric elements. Thus, each of the portions of a bar or sectors of a disc can be separate piezoelectric elements or constructed themselves from a combination of piezoelectric elements. It is also preferred to make the piezoelectric elements of the transducers, however constructed, resonant at approximately the frequency of the ultrasonic energy being handled by the transducers. This can be accomplished by making the long dimension of the bar 108 or the diameter of the disc 130 equal approximately to one wavelength, λ, of the ultrasonic energy.

Having thus described illustrative embodiments of improved ultrasonic energy transducers of the present invention, methods and apparatus for measuring the speed or velocity of ultrasonic energy in a moving web of material utilizing the transducers will now be described. For such measurement-operations, one or more ultrasonic transducers are contacted with a moving web of material. In one illustrative embodiment, ultrasonic transducers are incorporated into a measuring head 150 as shown in FIGS. 12 and 13.

One measuring head 150 or a plurality of measuring heads such as the measuring head 150 may be used at one or a plurality of locations across a web of material for measuring the speed or velocity of ultrasonic energy in a moving web and inferring strength characteristics of the web from the velocity measurements. However, it is currently preferred to incorporate the measuring head 150 into a sensor 152 or associate the measuring head 150 with the sensor 152. In this way, the measuring head 150 is scanned across a moving web 154 of material in conventional web scanning operations routinely used to measure characteristics of the web 154 of material as it is being manufactured, for example the basis weight of a paper web. See the arrangement illustrated in Fig. 14.

The illustrated measuring head 150 includes four cavities 56, 158, 160, 162 in its bottom of web engaging face. As illustrated, four transducers 164, 166, 168, 170 constructed in accordance with the third embodiment of FIGS. 5-6, are inserted into the cavities 156-162, respectively. The transducers 164-170 are sized and supported such that the material contacting means or dowels 126 are slightly recessed below the bottom face of the measuring head 150. The measuring head 150 includes a series of air passages 172 which terminate in air bearing openings 174 around the bottom face of the head 150 shown in FIG. 12.

Figure 13:
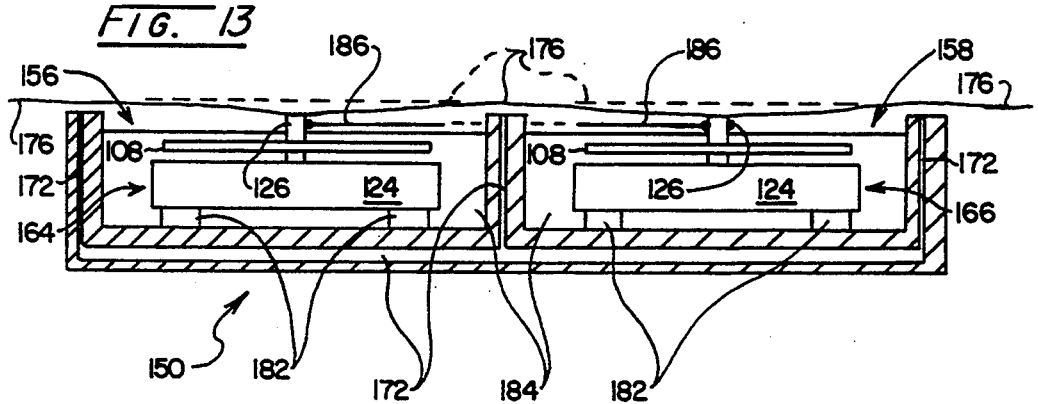
FIG. 13 is a sectional view taken along the section line 13—13 of FIG. 12.

As shown in FIG. 13, a web 176 of material moving past the head 150 is supported a distance from the bottom face of the head 150 by air flowing from the air bearing openings 174 therein. The web 176 can be selectively engaged with the transducers 164-170 or not dependent upon the application of vacuum to the cavities 156-162. Vacuum is applied to the cavities 156-162 or released by means of vacuum ports 178 formed into angularly inclined upper wall sections 180 of the cavities 156-162, see FIG. 12.

The transducers 164-170 are supported upon acoustic isolation pads 182 and the cavities 156-162 are filled to a level spaced from the bottom face of the measuring head 150 with a sound absorbing potting compound 184. In the illustrated embodiment, the transducer 164 is Set up to transmit ultrasonic energy through the web 176, or the web 154 of FIG. 14, and the transducers 166, 168, 170 are set up to receive ultrasonic energy from the web 176, or the web 154.

To compensate for electro-acoustic characteristics of the transducers 164-170, reference paths 186, 188, 190 are extended between the acoustic energy transmitting transducer 164 and the acoustic energy receiving transducers 166, 168, 170. In the illustrated embodiment of FIGS. 12 and 13, the reference paths 186, 188, 190 comprise quartz strands which are secured to the transducers 164-170 by means of an appropriate adhesive such as epoxy or otherwise. Of course other ultrasonic transmitting materials can be used to define the reference paths as will be apparent to those skilled in the art. An ultrasonic signal is then transmitted over the reference paths 186-190 to calibrate the transducers 164-170. The beginning point in time of transmitted ultrasonic energy is accurately identified by means of periodic calibration over a reference path. For example, for a measuring system wherein the measuring head is scanned across the web 154 of material being manufactured as generally shown in FIG. 14, the calibration may be performed once each scan. Of course, calibration can be performed more or less frequently as required for accurate web measurement.

While four transducers 164-170 are shown in the embodiment of the measuring head 150 of FIG. 12, it is currently preferred to utilize only three transducers in a web measuring system operable in accordance with the present invention. As shown schematically in FIG. 15, a first transducer 192 transmits ultrasonic energy through a web 194 of sheet material as it is being manufacturing and therefore is traveling in the direction of an arrow 196.

The transmitting transducer 192 is constructed in accordance with the foregoing teachings and description made relative to FIGS. 1-10. A signal generator 198 drives the transmitter 192 in response to activation signals received from a processor 200. When in contact with the web 194, the transducer 192 transmits a selectable number of cycles of ultrasonic energy through the web 194, four cycles currently being preferred. The frequency of the ultrasonic energy is selectable between approximately 40 kilohertz and 100 kilohertz with 60 kilohertz currently being preferred in view of resolution and size required for the system. The power P level of the drive signal produced by the signal generator 198, the number # of cycles of the signal and the frequency F can be selected by the processor 200. Alternately, as shown by dotted line inputs to the signal generator 198, these selections can be made by direct inputs.

In response to the drive signal generated by the signal generator 198 the first transducer 192 generates substantially pure longitudinal energy waves 202 fin the direction of a second transducer 204 and substantially pure shear energy waves 206 in the direction of a third transducer 208. The second and third transducers 204, 208 are constructed in accordance with the foregoing teachings and description made relative to FIGS. 1-10. The second transducer 204 is oriented to respond to the longitudinal energy waves 202 and the third transducer 208 is oriented to respond to the shear energy waves 206. The transducers 192, 204, 208 are supported in a housing 150', such as the housing 150 as previously described, to accomplish the noted transmission and reception of ultrasonic energy waves.

Reference path means, comprising in the illustrated embodiment a quartz strand 210 and a quartz strand 212, are coupled between the first transducer 192 and the second and third transducers 204, 208, respectively, for defining reference paths having known ultrasonic energy transmission characteristics therebetween.

As the energy waves are received by the transducers 204, 208, differential signals are generated by the transducers 204, 208 and passed to signal conditioning circuitry 214, 216. The resulting output signals from the Signal conditioning circuitry 214, 216 are passed to analog-to-digital (A/D) converters 218, 220. The A/D converters 218, 220 digitize the output signals from the signal conditioning circuitry 214, 216 and passed the resulting digital signals to the processor 200 where they are processed to determine the speed or velocity of ultrasonic energy in the web 194 of material.

It is possible and may reduce the circuitry and tolerances required of circuitry operation to multiplex the signals received from the transducers 204, 208. For a multiplex arrangement, all such Signals are processed by one channel such that any discrepancies between two signal processing channels are eliminated. Multiplexed operation and its advantages are well known in the art and will not be described further herein.

Figure 16:
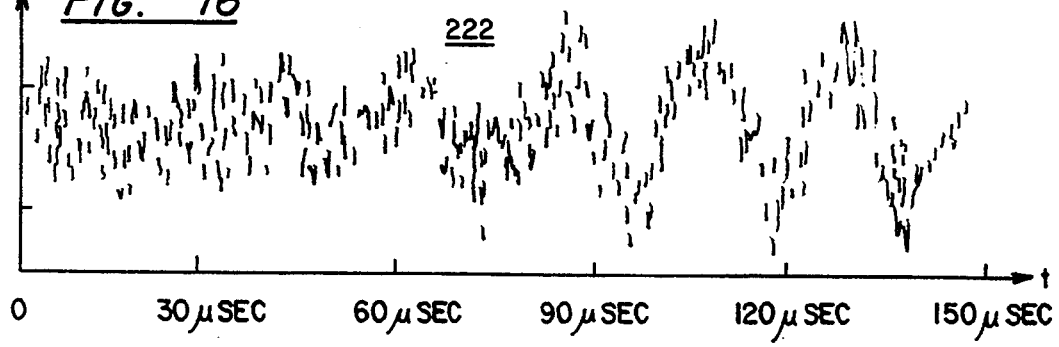
FIG. 16 is graph of an output signal for a single multiple cycle ultrasonic energy wave generated by a transducer used as a receiver for on-line measurement of a web of material.

Since the ultrasonic energy measurements are being taken as the transducers 192, 204 and 208 are in contact with and moving in both the machine direction and Cross direction, if scanned, relative to the web 194 of material, substantial noise results in output signals generated by the receivers 204, 208. The resulting noise is apparent in an output signal 222 generated by either the transducer 204 or the transducer 208 for a single received multiple cycle ultrasonic energy signal as shown in Fig. 16. The output signal 222 is the result of sampling the output signal of a transducer receiving a 60 kilohertz ultrasonic energy signal at a 5 megahertz sample rate with approximately 500 samples being shown in FIG. 16.

Figure 17:
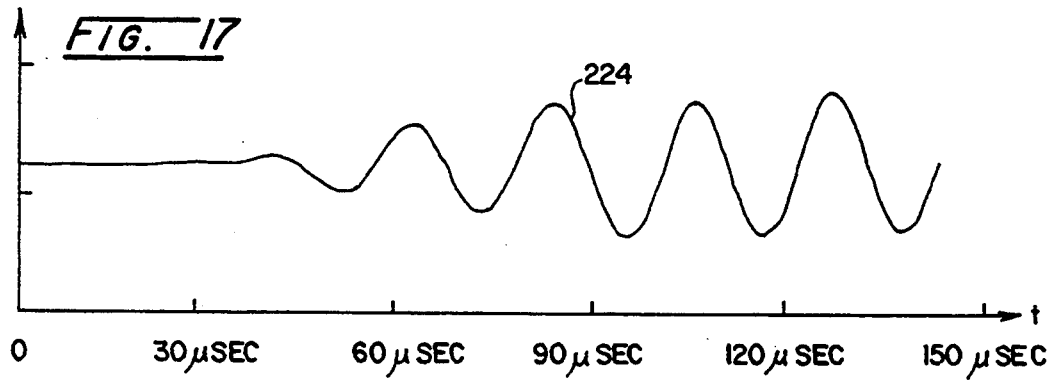
FIG. 17 is an integration of a relatively large number of output signals as shown in FIG. 16 with the noise substantially removed by the integration operation.

To extract the received ultrasonic energy waveform from the noise ladened samples making up the output signal 222 of FIG. 16, a large number of samples are taken and synchronously, digitally integrated, i.e. a large number of samples are summed and averaged. By integrating or summing and averaging a large number of individual samples making up a Corresponding number of output signals 222, for example 250 to 500, the randomly distributed noise generated by scanning the transducers 192, 204, 208 and by the web sliding at manufacturing velocity across the transducers 192, 204, 208, is substantially reduced resulting in a cleaned output signal 224 as shown in FIG. 17.

The operation of an on-line measuring system for measuring velocities of ultrasonic energy in webs of material as the webs are being manufactured will now be described with reference to the drawing figures and, in particular, FIGS. 14, 15, 18 and 19. The description will be for a single transmitting transducer, the transducer 192, and a single receiving transducer, the transducer 204, for ease of description. However, expansion to two or more receiving transducers. as well as variations of the control of the transmitting transducer will be apparent from this two transducer illustrative description.

A web manufacturing operation is in progress and the sensor 152 of a scanner system is being scanned back and forth across the web, such as the web 194, in the cross machine direction with the web moving in the machine direction. An on-line ultrasonic velocity measurement system in accordance with the present invention has been associated with the sensor 152, for example as shown in FIG. 14 by incorporation into the sensor 152.

Figure 19:
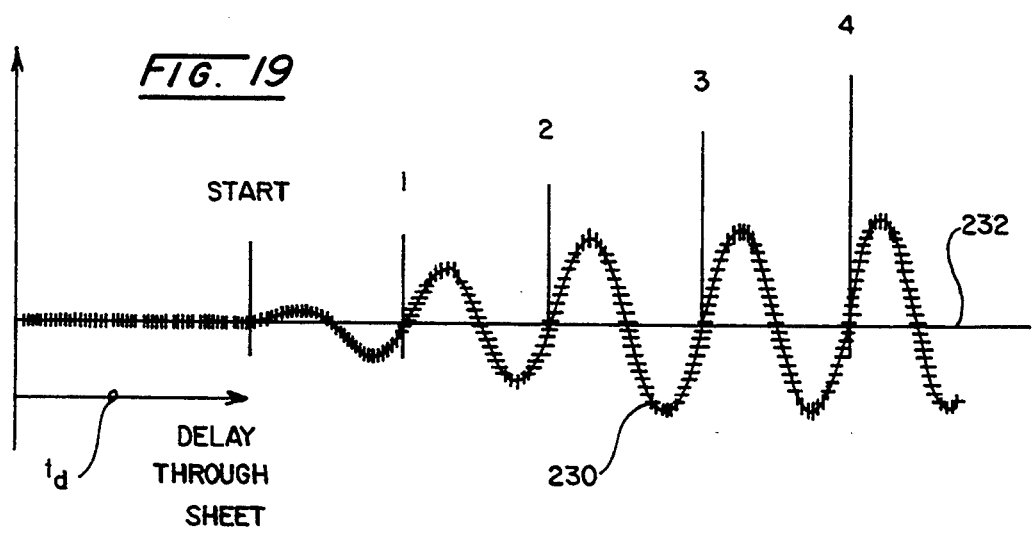
FIG. 19 is a graph of a digitally integrated series of received ultrasonic energy signals illustrating determination of average delay time of the signals through a web of material from which the velocity of the ultrasonic energy in the web is determined.

Initially vacuum is turned off to the measuring head 150' such that the head 150' and transducers 192, 204 contained within the head 150' are separated from the web 194 by an air bearing as previously described. As shown in FIG. 19, a trigger pulse 226 is generated by the processor 200 to activate the signal generator 198 to generate an ultrasonic energy signal comprising a selected number of cycles of a selected frequency ultrasonic energy, for example, four cycles of 60 kilohertz ultrasonic energy. In response to the trigger pulse 226, the ultrasonic energy signal is passed to the transducer 192.

Because of the electro-acoustic characteristics of the transmitting transducer 192, the ultrasonic energy signal does not instantaneously appear at the mechanical output of the transducer 192 but is delayed dependent upon the unique characteristics of the transducer 192. However, at some point in time O, the ultrasonic energy signal originates at the mechanical output of the transducer 192.

Since vacuum is not being applied to the head 150', the transducer 192 is not in contact with the web 194 and accordingly, no ultrasonic energy is transmitted through the web 194 by the transmitting transducer 192. However, the quartz strand 210 defines a reference path of known ultrasonic transmission characteristics between the transmitting transducer 192 and the receiving transducer 204. In this way, a calibration ultrasonic energy signal is transmitted to the receiving transducer 208 and received as an ultrasonic energy signal 228 shown ideally in FIG. 18.

Because of the electro-acoustic characteristics of the receiving transducer 204, the ultrasonic energy signal does not instantaneously appear at the electrical output of the transducer 204 but is delayed dependent upon the unique characteristics of the transducer 204. However, at some point in time $t_r$ the ultrasonic energy signal originates at the electrical output of the transducer 204.

Figure 18:
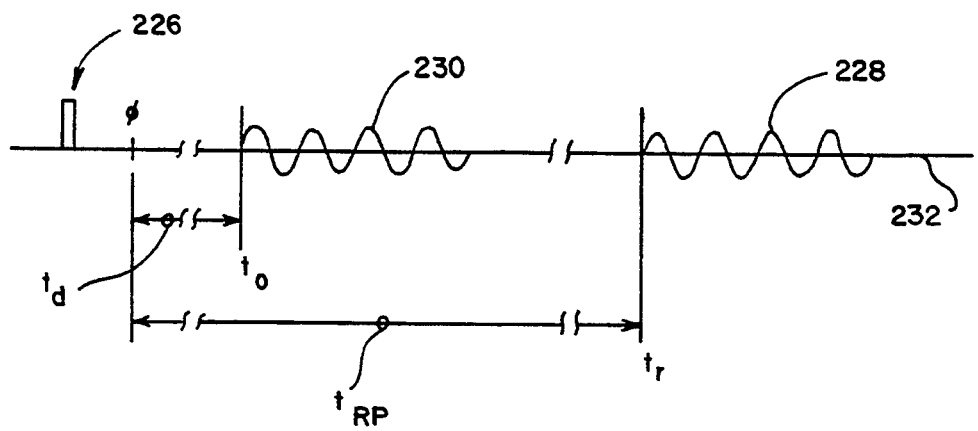
FIG. 18 is a schematic graphic representation illustrating operation of an on-line ultrasonic velocity measurement system for webs of material during manufacture.

Since the effective ultrasonic energy signal 228 is not a pure sine wave as shown in FIG. 18, its point of origin or the point in time $t_r$ is not entirely clear from the resulting signal. However, by knowing the frequency and number of cycles of ultrasonic energy which were transmitted, the processor 200 is able to determine the point in time $t_r$.

The determination of the point in time $t_r$ of the effective received ultrasonic energy signal can be performed by simply taking the data point which is closest to a baseline 232 of the signal. The point in time $t_r$ can also be determined by interpolating between a data point immediately above the baseline 232 and a data point immediately below the baseline 232. A least squares regression of points surrounding the point in time $t_r$ can also be used. These as well as other alternatives for determining the point in time $t_r$ of the effective received ultrasonic energy signal will be apparent to those skilled in the art.

Since the reference path has known ultrasonic energy transmission characteristics, the O time point of origin of the ultrasonic energy signal can be determined from the ultrasonic energy signal 228 received by the transducer 204 since it precedes the origin of the ultrasonic energy signal at the receiving transducer 204 by a determinable time $t_{RP}$.

The reference path is preferably made longer than the measurement path through the web of material such that the ultrasonic energy signal transmitted through the reference path does not interfere with ultrasonic velocity measurements of the web. The ultrasonic energy signal transmitted through the web does not interfere with the calibration signal since the transmitting transducer 192 and the receiving transducer 204 are not in contact with the web during calibration.

The ultrasonic energy signals do not immediately terminate upon termination of the ultrasonic energy signal generated by the signal generator 198. Accordingly, time must be allowed for the ultrasonic energy signals in the web and the reference path to dissipate or die away before another ultrasonic energy signal is produced. To assist in termination of the signals, the stud 118 and the extension of the dowel 126 between the piezoelectric element and its distal end 126a are preferably made equal to approximately one quarter of the wavelength of the ultrasonic energy signal, ¼λ. Termination of the ultrasonic energy signals is also assisted by making the long axis of the block 124 and the diameter of the disc 124' equal to approximately one wavelength of the ultrasonic energy signal, λ, which is preferred. Other damping arrangements, such as a lossy piezoelectric mounting or the like can be used in the present invention as will be apparent to those skilled in the art.

Figure 15:
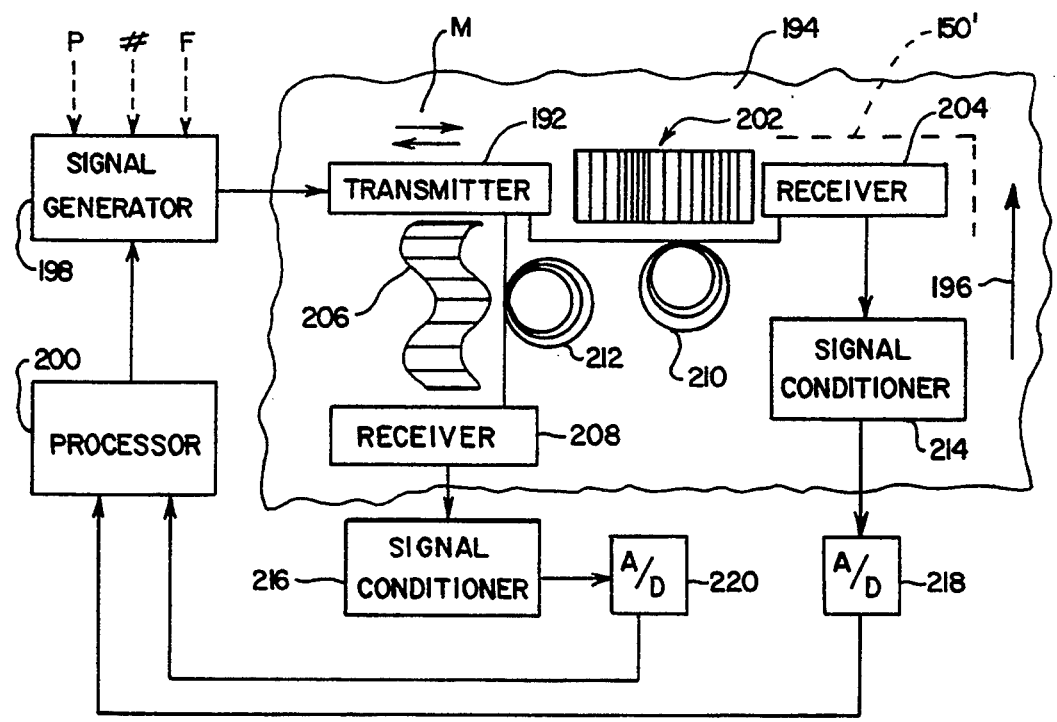
FIG. 15 is a schematic block diagram of an on-line ultrasonic velocity measuring system operable in accordance with the present invention to measure a web as it is being manufactured.

Once the origin point in time O has been determined via calibration through the reference path defined by the quartz strand 210 of FIG. 15, ultrasonic velocity measurements through the web 194 are performed. It is noted that by using a reference path, such as the quartz strand 210, the unique characteristic of both the transmitting transducer 192 and the receiving transducer 204 are used to determine the origin point in time O. It should be apparent that a reference path could be defined by simply touching the transmitting transducer 192 to the receiving transducer 204 if that were possible in a given application. Of course, with the transducers fixed in the measuring head 150' a separate and distinct reference path such as the quartz strand 210 must be provided.

To measure the velocity of ultrasonic energy through the web 194, vacuum is applied to the measuring head 150' such that the transducers 192, 204 are drawn into contact with the web 194 with the remainder of the web engaging face of the head 150' being borne by air as shown in FIG. 13. Ultrasonic energy signals are once again triggered by the processor 200, transmitted by the transducer 192, but now received by the transducer 204 after traveling through the web 194 of material which is being measured. A large plurality of ultrasonic energy signals are received by the transducer 204 and digitally integrated as previously described to result in an effective ultrasonic energy signal 230 as shown ideally in FIG. 18 and more accurately in FIG. 19. Due to the differences in the scanning speed of the sensor 152 and the speed of the web 194, the plurality of measurements are at substantially the same location across the web; however, the measurements extend over a length of web typically of one or two meters. This creates no problem since the web characteristics will normally be very consistent over such small lengths of the web in the machine direction.

Since the effective ultrasonic energy signal 230 is not a pure sine wave as shown in FIG. 18 but an increasing magnitude wave as shown in FIG. 19, its point of origin $t_o$ is not entirely clear from the resulting signal. However, by knowing the frequency and number of cycles of ultrasonic energy which were transmitted, the processor 200 is able to determine a sufficiently accurate point of origin $t_o$.

The determination of the point of origin $t_o$ of the effective received ultrasonic energy signal can be performed by simply taking the data point which is closest to the baseline 232 of the signal. The point of origin $t_o$ can also be determined by interpolating between a data point immediately above the baseline 232 and a data point immediately below the baseline 232. A least squares regression of points surrounding the point of origin $t_o$ can also be used. These as well as other alternatives for determining the point of origin $t_o$ of the effective received ultrasonic energy signal will be apparent to those skilled in the art.

In any event, once the point of origin $t_o$ is determined, the delay time through the sheet $t_d$ can be determined by relation to the origin point in time O at which the ultrasonic energy signal originated. Using the delay time through the sheet $t_d$ and the distance between the transmitting transducer 192 and the receiving transducer 204, the processor is able to determine the velocity of the ultrasonic energy through the web 194. The determined velocity is used in a well known manner to determine characteristics of the web 194 of sheet material. The characteristics so determined can be recorded, used to control the manufacturing process producing the web 194 and/or displayed to an operator of the process.

The described operation of a system for measuring the velocity of ultrasonic energy in a web of material as it is being measured is highly accurate. However, some degree of error is introduced due to variations in the interface of individual transducers to the web 194 of material which is being measured. While it is not necessary for the highly reliable and accurate measurement of the velocity of ultrasonic energy in a moving web of material as it is being manufactured, it is believed that such errors can be corrected by empirical adjustments of the measurement results dependent upon the characteristics of the interface. For example, it is believed that correction tables or factors can be developed for different grades of paper to further improve the accuracy of measurements made using the present invention.

Having thus described the methods and apparatus of the present invention in detail and by reference to preferred embodiments-thereof, it will be apparent that modifications and variations are possible without departing from the scope of the invention defined in the appended claims.

What is claimed is:

1. Apparatus for use in a system for on-line measurement of velocities of ultrasonic energy in sheet material comprising:
    a first transducer for transmitting ultrasonic energy through said sheet material during manufacture of said sheet material;
    a second transducer for receiving ultrasonic energy from said sheet material during manufacture of said sheet material;
    a housing for supporting said first and second transducers in a defined orientation relative to one another for engagement with said sheet material during manufacture of said sheet material; and
    a first reference path device coupled between said first transducer and said second transducer for providing a reference path having known ultrasonic energy transmission characteristics between said first and second transducers.

2. Apparatus for use in a system for on-line measurement of velocities of ultrasonic energy in sheet material as claimed in claim 1 wherein said first reference path device comprises a quartz strand.

3. Apparatus for use in a system for on-line measurement of velocities of ultrasonic energy in sheet material as claimed in claim 1 further comprising:
    a third transducer for receiving ultrasonic energy from said sheet material during manufacture of said sheet material, said housing further providing for supporting said third transducer in a defined orientation relative to said first and second transducers for engagement with said sheet material during manufacture thereof; and a second reference path device coupled between said first transducer and said third transducer for providing a refer path having known ultrasonic energy transmission characteristics between said first and third transducers.

4. Apparatus for use in a system for on-line measurement of velocities of ultrasonic energy in sheet material as claimed in claim 3 wherein said first and second reference path devices each comprise a quartz strand.

5. Apparatus for use in a system for on-line measurement of velocities of ultrasonic energy in sheet material as claimed in claim 3 wherein said housing comprises an air berating device for supporting said housing on said sheet material.

6. Apparatus for use in a system for on-line measurement of velocities of ultrasonic energy in sheet material as claimed in claim 5 wherein said housing further comprises a sheet engagement apparatus for selectively engaging said first, second and third transducers with said sheet material.

7. Apparatus for use in a system for on-line measurement of velocities of ultrasonic energy in sheet material as claimed in claim 6 wherein said sheet engagement apparatus. comprises a vacuum applier for drawing said sheet material to said first, second and third transducers.

8. Apparatus for use in a system for on-line measurement of velocities of ultrasonic energy in sheet material as claimed in claim 7 further comprising a driver circuit for driving said first transducer to transmit a selectable number of cycles of defined frequency ultrasonic energy.

9. Apparatus for use in a system for on-line measurement of velocities of ultrasonic energy in sheet material as claimed in claim 8 further comprising a processor for receiving-signals representative of said ultrasonic energy from said second and third transducers and identifying said selectable number of cycles of said defined frequency ultrasonic energy.

10. A method of on-line measurement of velocities of ultrasonic energy in sheet material comprising the steps of:

(a) providing a first transducer for transmitting ultrasonic energy through sheet material as said sheet material is being manufactured;

(b) providing a second transducer for receiving ultrasonic energy from said sheet material, said second transducer being positioned a known distance from said first transducer;

(c) calibrating said first and second transducers via a reference path coupled therebetween to determine a time of origination of ultrasonic energy transmitted through said sheet material by said first transducer, said reference path having known ultrasonic energy transmission characteristics;

(d) engaging said first and second transducers with said sheet material;

(e) transmitting a first selected number of cycles of defined frequency ultrasonic energy through said sheet material via said first transducer;

(f) receiving said first selected number of cycles of defined frequency ultrasonic energy from said sheet material via said second transducer;

(g) determining the time of receipt of an origination point of said first selected number of cycles of defined frequency ultrasonic energy; and (h) determining the velocity of said ultrasonic energy from the known distance of said second transducer from said first transducer and the origination point of said first selected number of cycles of defined frequency ultrasonic energy.

11. A method of on-line measurement of velocities of ultrasonic energy in sheet material as claimed in claim 10 wherein step (c) of calibrating said first and second transducers via a reference path coupled therebetween comprises the steps of:

(i) transmitting a second selected number of cycles of defined frequency ultrasonic energy through said reference path via said first transducer;

(j) receiving said second selected number of cycles of defined frequency ultrasonic energy from said reference path via said second transducer; and (k) determining the time of receipt of an origination point of said second selected number of cycles of defined frequency ultrasonic energy, 12. A method of on-line measurement of velocities of ultrasonic energy in sheet material as claimed in claim 11 wherein Said first and second selected numbers of cycles are equal to one another.

* * * * *

UNITED STATES PATENT AND TRADEMARK OFFICE
CERTIFICATE OF CORRECTION

PATENT NO. : 5,398,538
DATED : March 21, 1995
INVENTOR(S) : Williams et al.

It is certified that error appears in the above-indentified patent and that said Letters Patent is hereby corrected as shown below:

Col. 19, Line 5, "a refer path" should be
  --a reference path--.

Col. 19, Line 16, "air berating device" should be
  --air bearing device--.

Col. 19, Line 41, "receiving-signals" should be
  --receiving signals--.

Col. 20, Line 43, "ultrasonic energy," should be
  --ultrasonic energy.--.

Col. 20, Line 46, "wherein Said first" should be
  --wherein said first--.

Col. 19, Line 29, "apparatus. comprises" should be
  --apparatus comprises--.

Signed and Sealed this

Fourth Day of July, 1995

*Attest:*

BRUCE LEHMAN

*Attesting Officer*   Commissioner of Patents and Trademarks